United States Patent [19]
McRae

[11] Patent Number: 5,807,278
[45] Date of Patent: Sep. 15, 1998

[54] NONINVASIVE BLADDER PRESSURE AND URINE FLOW MEASUREMENT APPARATUS AND METHOD

[76] Inventor: Lorin P. McRae, P.O. Box 309, Oracle, Ariz. 85623

[21] Appl. No.: 656,943

[22] Filed: Jun. 6, 1996

[51] Int. Cl.⁶ ..................................................... A61B 5/00
[52] U.S. Cl. .......................... 600/579; 600/574; 600/573; 604/349; 604/352
[58] Field of Search .................................... 128/760, 762, 128/766; 604/317, 349, 351, 352, 353; 606/240; 601/152, 153; 600/573, 574, 575, 579, 578

[56] References Cited

U.S. PATENT DOCUMENTS

| | | | |
|---|---|---|---|
| 2,699,781 | 1/1955 | Koch | 604/352 |
| 2,896,612 | 7/1959 | Bates et al. | 601/152 |
| 3,353,538 | 11/1967 | Carrigan | 604/352 |
| 3,511,241 | 5/1970 | Lee | 604/352 |
| 4,343,316 | 8/1982 | Jespersen | 128/762 |
| 4,516,568 | 5/1985 | Baxter et al. | 606/240 |
| 5,062,304 | 11/1991 | Van Buskirk et al. | 128/760 |
| 5,377,101 | 12/1994 | Rollema | 128/760 |
| 5,396,894 | 3/1995 | Eide et al. | 128/686 |
| 5,409,014 | 4/1995 | Napoli et al. | 128/762 |
| 5,616,138 | 4/1997 | Propp | 604/317 |

*Primary Examiner*—Lynne A. Reichard
*Assistant Examiner*—Justine R. Yu
*Attorney, Agent, or Firm*—J. Winslow Young

[57] ABSTRACT

A noninvasive bladder pressure and urinary flow measurement apparatus and method, the apparatus including a pressure cuff configured to be removably mounted to the penis of the patient and an inflation system for selectively inflating and deflating the pressure cuff. A urine collection and measurement system is provided to measure the volume and rate of urine discharged by the patient. The transient response also provides an indication whether a constriction of the urethra is proximal or distal.

4 Claims, 1 Drawing Sheet

NONINVASIVE BLADDER PRESSURE AND URINE FLOW MEASUREMENT APPARATUS AND METHOD

BACKGROUND

1. Field of the Invention

This invention relates to apparatus for testing bladder pressure and urinary flow and, more particularly, to a novel, noninvasive apparatus and method for testing bladder pressure and urinary flow to aid in the diagnosis and evaluation of patients with existing or potential urological disorders, primarily prostate pathology.

2. The Prior Art

The prostate is a muscular, walnut-shaped gland about an inch and a half long and resides directly below the bladder. One of functions of the prostate is to produce a portion of the fluid that constitutes semen, the fluid that transports sperm. During orgasm the muscles of the prostate contract and force this fluid into the urethra. Since the prostate encircles the urethra it is in position to adversely affect the outflow of urine from the bladder. As a man ages, characteristic changes begin to occur in the prostate. For example, the aging prostate becomes more sensitive to smaller amounts of the male sex hormone, testosterone, leading some researchers to believe that estrogen plus aging equals a prostate easily influenced by testosterone, even when there is less of it in the body. In other words, the threshold for hormone influence is lowered. At birth the prostate is quite small but enlarges considerably from puberty to about age 20 where it reaches what is considered to be its normal size.

At approximately age 40, the prostrate begins to enlarge with the result that anywhere from 10 to 30 percent of these men eventually will require treatment to relieve symptoms of difficult and/or restricted urination, incomplete bladder emptying or other associated pathology. Rarely does the prostate present a major problem before age 50, although certain changes may have been occurring as early as at least age 40. The prostate may become cancerous and, if untreated, the cancer could spread beyond the gland to other organs and ultimately prove terminal.

Benign prostatic hypertrophy (BPH) is an enlargement of the prostate tissue, though not cancerous. An enlargement of the prostate, whether cancerous or not, tends to restrict urine flow during the voiding process, micturition. As in other fluids, urine follows the hydrodynamic concept that in order for flow to occur, the urine must be subjected to a pressure differential, that is, internal pressure must be greater than any restrictions to flow. At the start of micturition, the bladder generates an internal pressure sufficient to accelerate the urine toward the exterior. Once fluid motion is established, the bladder, by its contraction, continues to exert sufficient pressure on the urine to overcome all energy loss mechanisms in the urethra at a level sufficient to maintain urinary flow. The greatest impediment to flow usually lies in the tightest portion of the urethra at a segment called the flow control zone, which in the human male lies in that region of the prostate between the bladder neck and the membranous urethra. In short, the prostate resides within and thus can adversely affect the flow of urine through this flow control zone.

Benign prostatic hypertrophy is, therefore, a prominent health issue that affects micturition. Treatment for a patient who has been evaluated to be thus obstructed can involve a range of treatment protocols ranging from watchful waiting to the use of medications and, in the more extreme cases, surgery. While other non-surgical medical treatments are receiving increased attention (as are a wide variety of laser, balloon dilation, and non-traditional surgical approaches) surgery remains the principle treatment for this type of prostatic problem. The surgery for BPH, where the prostrate is abnormally large but not cancerous, varies from that of cancer surgery and is typically less traumatic to the patient. The instances of BPH are significantly more common than prostatic cancer. During 1990, diagnoses for BPH outnumbered those for prostate cancer in U.S. short stay, non-Federal hospitals by more than two to one. Prostate disease is expected to become more and more prevalent as longevity increases among U.S. men.

The typical surgery for benign prostrate hypertrophy involves only a partial removal of prostatic tissue and is directed toward relieving bladder outlet obstruction. While surgery for BPH can be helpful to reduce problematic symptoms for patients who are truly obstructed, accurate diagnosis of patients thus obstructed is difficult. Thus, surgical relief of prostate obstruction due to BPH has become one of the most common surgical procedures although without a good indicator of which patients will appropriately benefit. Several studies have demonstrated that traditional clinical methods to determine objective need for prostate surgery are not conclusive in determining the severity of obstruction. Historically, clinical investigations include study of family history, evaluation of prostate size as estimated with conventional methods such as rectal palpation, prostate ultrasound, existence of residual urine, visualization of prostatic tissue, as well as other methods. These above-mentioned methods are not conclusive relating the degree of obstruction to the prostate. Notably, a review of the various forms of treatment indicate that up to 30% of the patients diagnosed as having BPH by the foregoing methods and who undergo surgery, did not receive the expected benefits. Studies indicate that approximately 30% of the patients undergoing surgery for BPH did not experience a significant reduction of volume of residual bladder urine after the operation. The conclusion was that a prostatic operation for this group could probably have been avoided. The foregoing conclusion is particularly noteworthy in light of the associated surgical complications of incontinence (up to 1.2%) constriction of the urethra (12%), bladder neck narrowing or constriction (greater than 15%), loss of ejaculation (55%), and impotence (12%). Also, the possibility of a second operation being necessary after 8 years is between 10.1% and 20.2%, depending on the type of surgery performed. Moreover, the mortality rate of between 0.1% and 9.0% suggests that the surgery cannot be viewed as a low risk or minor surgery. Therefore, it is of the greatest importance to prove objectively whether a patient has a bladder outlet obstruction due to the prostrate enlargement, or if his pathology is due to other factors such as urethra irritability, bladder limitations, or impaired capability of the muscle (the detrusor) that assists with the expulsion process. For these patients, pharmacological treatment or temporary bladder drainage by a catheter is possibly indicated.

Historically, methods to detect prostate pathology include a digital rectal examination, where a doctor inserts a gloved and lubricated finger into the patient's rectum to palpate the prostate gland, determining if the prostate seems enlarged, hard or bumpy. This procedure may be followed by performance of a biopsy of the prostate tissue if cancer is suspect. Blood tests provide some indication if cancer has invaded the prostate gland by measurement of the amount of an antigen emitted by the prostate. However, it is much more difficult to determine BPH where cancer is not present or even suspect. Even though a patient is experiencing symptoms of difficultly in initiating urinary flow, decrease in volume urinary flow, or residual bladder urine after an attempt to empty, BPH is not always indicated. Other possibilities for the above stated symptoms are urethra irritability, bladder limitations, an impaired detrusor, or a secondary constriction (more distal to bladder).

Evaluation of obstruction of urinary flow due to BPH includes methods that evaluate flow rate, volume voided, bladder pressure, and an analysis of the location of any restriction to flow. Prior art tests include having the patient void against a rotation disk flow transducer to measure flow. Measurement of cast distance as an indicator of bladder pressure and a check for restriction to flow. Flow and volume have also been determined by suprapubic puncture to measure the bladder pressure while voiding around an indwelling catheter. These prior art procedures are complex, uncomfortable, and/or do not provide sufficiently accurate data to enable the caregiver to determine if surgery would provide a decrease in problematic symptoms. While certain invasive methods can provide more accurate data than stream studies, artifacts can be introduced, and the tests are uncomfortable. Further, determination of a constriction to the urethra at the prostate is not conclusive simply by analysis of stream velocity alone. For example, as when there are two constrictions to flow (one proximal, one distal to the bladder), and where flow equilibrium occurs between the two constrictions, inadequate data will not enable one to quantify the constriction at the proximal location exclusively, i.e., at the prostate gland. This inaccuracy of data is due to the urine introduced at the proximal end passing the first constriction as a jet and then flow to the distal constriction where the urine is backed up, to a degree. Accordingly, if there are two constrictions, one proximal to the bladder at the prostate and one distal, determination of degree of constriction at the prostate cannot be determined with conventional catheter methods.

Importantly, risks and difficulty for prior art invasive methods are greatest for males who have a severely obstructed prostate, the very population for which objective testing would be most desirable. Another factor requiring careful consideration when dealing with BPH is the fact of the relatively recent advances in the discovery of medications that may be available for the treatment of BPH symptoms. Accordingly, there will be an even greater demand for a simple, noninvasive test that can be used to accurately evaluate the effectiveness of this treatment protocol. Further, even the benign process known in the art as "watchful waiting" could significantly benefit from a suitable, noninvasive, yet accurate, evaluation of bladder pressure and urinary flow. Finally, because of the inaccuracy of test results of these prior art methods, as well as associated expenses and risks, physicians most often make qualitative evaluations based on experience and symptom scoring, which leads to the performance of many (as high as 30%) unnecessary surgical procedures, making it neither practical nor safe to perform such procedures in a routine manner.

In view of the foregoing, it would be a significant advancement in the art to provide an apparatus and method that would more accurately measure bladder pressure and urinary flow. It would also be an advancement in the art to provide a bladder pressure and urinary flow apparatus and method that could be performed in a noninvasive manner. An even further advancement in the art would be to provide a bladder pressure and urinary flow apparatus and method that would more accurately aid in determining the location of a constriction. Such a novel invention is disclosed and claimed herein.

BRIEF SUMMARY AND OBJECTS OF THE INVENTION

This invention is a novel, noninvasive bladder pressure and urinary flow measurement apparatus and method. The apparatus includes an occluding pressure cuff, pressure dial, bulb inflator, a release button, a rate and volume measurement system, a data recorder and associated connection tubing. The method is practiced by placing the pressure cuff on the penis adjacent the glans where, upon inflation, the pressure cuff is used to selectively constrict the urethra. Pressure and flow rates are then determined to provide an indication of the degree to which the prostate has obstructed the urethra thereby aiding in the diagnosis of benign prostatic hypertrophy. In the event there is a constriction in the urethra, an analysis of the transient response provides a reliable indication as to the location of that constriction.

It is, therefore, a primary object of this invention to provide improvements in apparatus for the diagnosis of benign prostatic hypertrophy.

Another object of this invention is to provide improvements in the method of determining bladder function as it relates to benign prostatic hypertrophy.

Another object of this invention is to provide a bladder pressure and urinary flow apparatus that is noninvasive.

Another object of this invention is to provide a bladder pressure and urinary flow apparatus that could be performed by persons other than surgically licensed personnel.

Another object of this invention is to provide a bladder pressure and urinary flow apparatus that would provide improvements in locating position of constriction to urinary flow.

These and other objects and features of the present invention will become more readily apparent from the following description in which preferred and other embodiments of the invention have been set forth in conjunction with the accompanying drawing and appended claims.

BRIEF DESCRIPTION OF THE DRAWING

The drawing is a plan view of the noninvasive bladder pressure and urinary flow apparatus of this invention shown in the environment of male genitalia which is illustrated schematically for ease of understanding.

DETAILED DESCRIPTION OF THE PREFERRED EMBODIMENT

Figure 1:
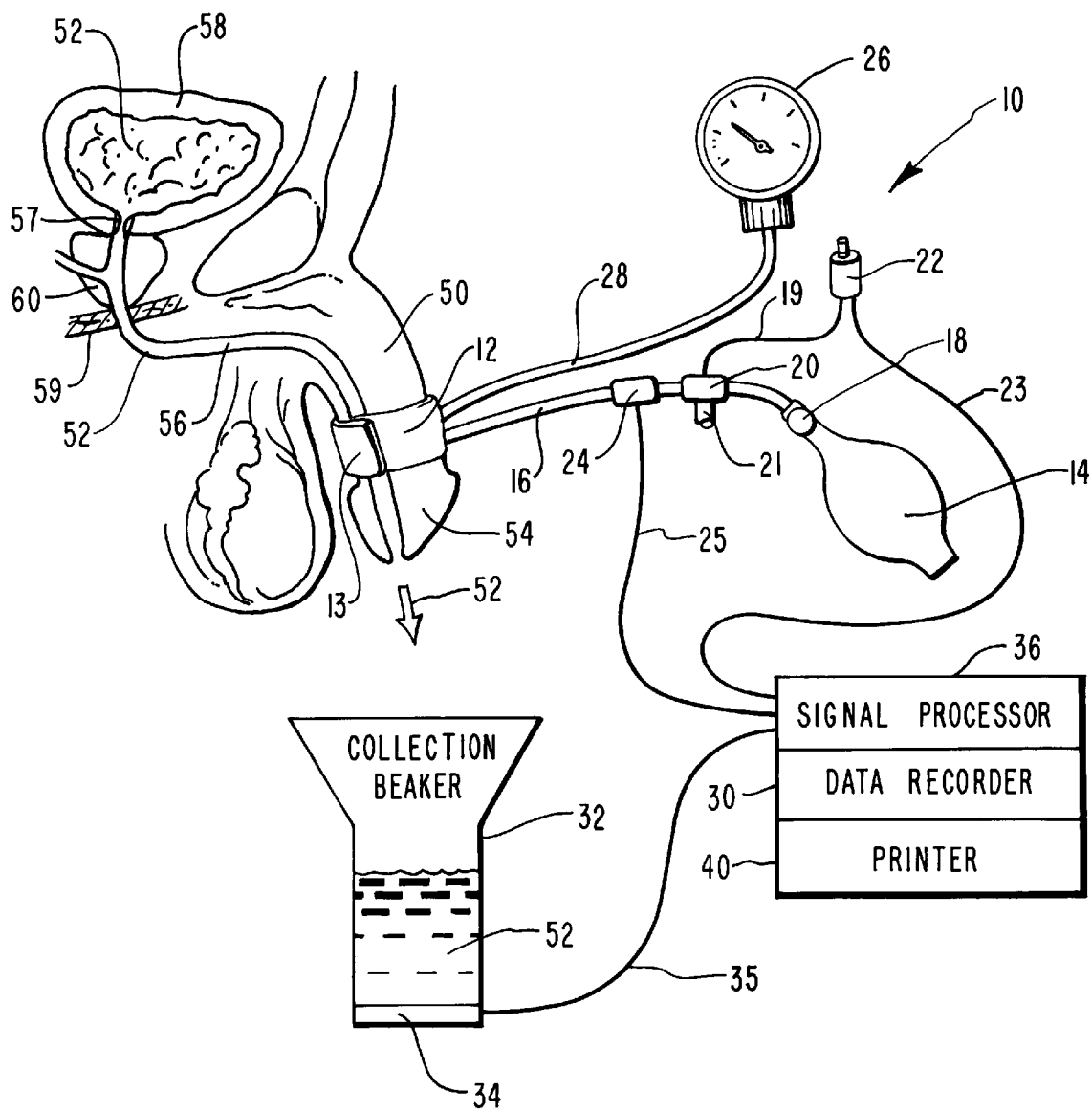

The invention is best understood from the following description with reference to the drawing wherein like parts are designated by like numerals throughout and taken in conjunction with the appended claims.

GENERAL DISCUSSION

The underlying rationale for a noninvasive apparatus and method of this invention for performing bladder pressure and urinary flow analysis is to (a) decrease the risks and difficulty in performing evaluation testing and diagnosis of patients experiencing urological disorders; (b) increase the accuracy of testing to determine severity of constriction to urinary flow; (c) make it possible for bladder pressure and urinary flow testing to be performed by persons other than surgically licensed personnel; and (d) provide improvements in locating the position of constriction of urinary flow. The difficulty of achieving an accurate diagnosis of urological patients whose urological constriction may be due to prostate enlargement, using prior art methods of stream studies or invasive methods, is evidenced by the high percentage of patients who are not adequately tested prior to surgery or who do not gain expected results after undergoing of prostatic surgery. Not all clinical methods for measuring fluid pressure are invasive. For example, blood pressure has long been measured noninvasively using an occluding pressure cuff and a means of determining high and low pressures as the cuff pressure is slowly released. Static (no-flow) bladder pressure in males can be measured using the same technique with an occlusive pressure cuff on the penis. The pressure in the bladder differs from the pressure against the cuff only by the elevation of the bladder above the cuff. This distance can be measured or estimated and subtracted from the cuff pressure. The bladder and cuff pressure are subject to similar considerations as manual blood pressure testing.

Specifically, a pressure cuff is secured to the penis shaft adjacent the glans where it is inflated until it constricts the urethra sufficiently to prevent the flow of urine. The patient is instructed to attempt micturition (which releases the internal sphincter and exerts pressure on the bladder) while at the same time slowly releasing pressure in the cuff. The point at which urine commences to flow is the pressure at which the pressure exerted on the bladder is sufficient to overcome the constrictive pressure in the cuff. The pressure in the cuff is then rapidly released in order for full urine flow to commence. The rate and total quantity of urine discharge are also measured and, along with bladder pressure, provides to the clinician a fairly accurate determination of the condition of the prostrate as it affects the output of urine through the urethra.

The noninvasive method of measuring bladder pressure and flow of this invention makes possible more accurate determination of the location of any constriction of the urethra. Specifically, the transient flowrate waveform generated at the time of pressure release from the cuff differentiates a proximal obstruction as from the prostate from a distal obstruction such as stenosis of the meatus. Further, the novel, noninvasive bladder pressure and urinary flow measurement apparatus and method of this invention provides to the caregiver a quantitative, noninvasive evaluation of detrusor strength and urinary flow obstruction which will enable better evaluation of response to medication and a higher level of accurate data for use during watchful waiting for male urinary disease.

DETAILED DESCRIPTION

Referring now to the drawing, the novel bladder pressure and urinary flow measurement apparatus of this invention is shown generally as instrumentation 10 in the environment of a penis 50. Instrumentation 10 includes a cuff 12, an inflator 14, an inflation tube 16, a control valve 18, a quick release valve 20, a quick release switch 22, a pressure sensor 24, a pressure gauge 26, and a pressure tube 28. Instrumentation 10 also includes a signal processor 36, a data recorder 30, and a printer 40. A collection beaker 32 is mounted on a strain gauge 34 which is electrically coupled to signal processor 36 through a wire 35. Signal processor 36 determines the volume and rate of flow of a urine 52 collected in collection beaker 32. Signal processor also receives pressure signals from pressure sensor 24 through wire 25 and transmits a release signal to quick release switch 22 through wire 23 as will be described more fully hereinafter.

Quick release switch 22 can be used to manually operate quick release valve 20 through a wire 19. A vent 21 on quick release valve 20 provides for the rapid deflation of cuff 12 as will be discussed more fully hereinafter. Cuff 12 is configured with an overlap section 13 having a hook and loop fastener system for releasably engaging cuff 12 about penis 50. The entire pneumatic circuitry of cuff 12, inflation tube 16, and pressure tube 28 constitutes a single pressure circuit with the pressure therein created through the use of inflator 14 and control valve 18. The pressure therein is visually displayed by pressure gauge 26 and sensed by pressure sensor 24. Control valve 18 is a slow release valve, the function of which will be described more fully hereinafter.

Collection beaker 32 is placed below penis 50 to collect urine 52 discharged therefrom during the practice of this invention as will be discussed more fully hereinafter. Collection beaker 32 is supported on strain gauge 34 which, in turn, is electrically coupled to signal processor 36 by wire 35. Signal processor 36 determines the flow rate of urine 52 from the volume of urine 52 collected in collection beaker 32 as sensed by strain gauge 34 and measured against time. This flow rate information is stored in data recorder 30.

The anatomy associated with penis 50 includes a glans 54 at the distal end of penis 50 and a urethra 56 extending the length of penis 50 at a starting point at a bladder 58 and exiting through an orifice in glans 54. A prostate 60 encircles urethra 56 adjacent bladder 58 where it can cause undue constriction of urethra 56 thereby creating problems with the discharge of urine 52 along with interference with the complete emptying of bladder 58. An involuntary, internal sphincter 57 at the junction of urethra 56 with bladder 58 releases upon contraction of bladder 58 to allow urine 52 to flow into urethra 56 from bladder 58. A voluntary, external sphincter 59 immediately distal of prostate 60 can be controlled by the patient to stop flow of urine 52.

THE METHOD

In practicing the method of this invention the patient, for whom the functioning of bladder 58, urethra 56, and prostate 60 is to be determined, is instructed to drink approximately one liter of water commencing about one hour prior to testing. The patient or an attendant then engages cuff 12 to penis 50 adjacent glans 54. Cuff 12 is sufficiently loose at this juncture so as to not impede the flow of urine 52 through urethra 56. When the patient senses a full bladder and has the urge to micturate the patient or the attendant (not shown) adjusts control valve 18 and squeezes inflator 14 to cause cuff 12 to constrict penis 50 sufficiently to prevent all flow of urine 52 through urethra 56, usually at a pressure of about 230 cm of water. The patient is then instructed to urinate or, rather, attempt to micturate thus creating increased pressure on bladder 58 and a release of sphincters 57 and 59 while at the same time slowly releasing pressure in cuff 12 through control valve 18. At a certain point the pressure in cuff 12 will fall to a pressure that can be overcome by the pressure imposed on urine 52 such that a few drops of urine 52 will be discharged into collection beaker 32. At that point quick release switch 22 is either manually operated or electronically activated by signal processor 36 to open quick release valve 20 to vent pressure in cuff 12 through vent 21. This rapid release of cuff 12 allows the patient to discharge urine 52 from bladder 58 directly into collection beaker 32. Strain gauge 32 senses the increase in weight of collection beaker 32 from the volume of urine 52 collected therein and transmits this information to signal processor 36 through wire 35. Signal processor 36 determines the volume and rate of flow of urine 52 and transmits this data to data recorder 30. This information along with the pressure information obtained by pressure sensor 24 provides to the medical professional (not shown) a fairly comprehensive picture of the degree to which, if any, prostate 60 impedes the outflow of urine 52 from bladder 58 and the degree to which residual urine is retained in bladder 58. Accordingly, the apparatus and method of instrumentation 10 provides a simple, non-invasive technique for detecting the onset of BPH and for evaluating the degree of its severity. Importantly, instrumentation 10 completely avoids the insertion of any devices through urethra 56 into bladder 58 thereby effectively eliminating any injury to urethra 56 and also avoiding the inadvertent introduction of infectious organisms into bladder 58.

The transient response from the time of rapid release of cuff 12 until full flow of urine 52 is sensed by pressure transducer 34, as determined by signal processor 36, provides valuable information about the location of any constriction in urethra 56. The waveform of this transient response, as sensed by signal processor 36, reveals the general location of the obstruction. For example, if the waveform has a spike in it, the obstruction is proximal whereas the absence of a spike indicates that the obstruction is distal. This waveform is visually displayed by the printout produced from printer 40.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for determining bladder function in a human male patient comprising the steps of:
    placing an inflatable cuff about the penis of the human male;
    inflating said inflatable cuff with sufficient pressure to cause said inflatable cuff to prevent flow of urine through the urethra in the penis;
    releasing said pressure gradually while the patient is exerting force on the bladder until said force is sufficient to overcome said pressure to initiate urine flow through the urethra;
    venting said pressure rapidly from said inflatable cuff thereby allowing urine to flow freely under said force;
    collecting the urine while measuring the rate of flow and volume of urine discharged from the bladder; and
    recording said pressure, said rate of flow, and said volume.

2. The method defined in claim 1 wherein said inflating step includes connecting a pressure gauge to said inflatable cuff thereby providing a visual readout of said pressure.

3. The method defined in claim 1 wherein said releasing step includes noting said pressure at said urine flow as a function of the pressure exerted on the bladder by said force.

4. The method defined in claim 1 wherein said collecting step includes providing a vessel for collecting said urine and mounting said vessel on a strain gauge, said strain gauge measuring the volume of urine and the rate of urine in said vessel.

* * * * *